(12) United States Patent
Kesten et al.

(10) Patent No.: US 9,757,018 B2
(45) Date of Patent: Sep. 12, 2017

(54) MEDICAL GUIDEWIRE WITH INTEGRAL LIGHT TRANSMISSION

(71) Applicant: Acclarent, Inc., Menlo Park, CA (US)

(72) Inventors: Randy J. Kesten, Mountain View, CA (US); Thomas R. Jenkins, Alameda, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 14/824,528

(22) Filed: Aug. 12, 2015

(65) Prior Publication Data
US 2016/0287062 A1 Oct. 6, 2016

Related U.S. Application Data

(60) Provisional application No. 62/140,740, filed on Mar. 31, 2015.

(51) Int. Cl.
| | |
|---|---|
| A61B 5/00 | (2006.01) |
| A61B 1/06 | (2006.01) |
| A61M 25/09 | (2006.01) |
| A61B 1/01 | (2006.01) |
| A61L 31/02 | (2006.01) |
| A61M 25/01 | (2006.01) |
| G02B 6/02 | (2006.01) |

(Continued)

(52) U.S. Cl.
CPC .............. *A61B 1/0676* (2013.01); *A61B 1/01* (2013.01); *A61B 5/0084* (2013.01); *A61B 5/065* (2013.01); *A61L 31/022* (2013.01); *A61M 25/0105* (2013.01); *A61M 25/09* (2013.01); *G02B 6/02* (2013.01); *A61M 2025/09075* (2013.01); *A61M 2210/0618* (2013.01); *A61M 2210/0681* (2013.01); *G02B 23/24* (2013.01)

(58) Field of Classification Search
CPC ........ A61M 25/09; A61M 2025/09075; A61M 2025/09083; A61M 2025/09091
USPC .......................................................... 600/585
See application file for complete search history.

(56) References Cited

U.S. PATENT DOCUMENTS

| | | | |
|---|---|---|---|
| 5,651,783 A | 7/1997 | Reynard | |
| 6,458,088 B1 * | 10/2002 | Hurtak ................. | A61M 25/09 600/585 |

(Continued)

FOREIGN PATENT DOCUMENTS

WO WO 2009/116969 9/2009

OTHER PUBLICATIONS

U.S. Appl. No. 62/140,740, filed Mar. 31, 2015.
International Search Report and Written Opinion dated Jun. 13, 20216 re Application No. PCT/US2016/024731.

*Primary Examiner* — Max Hindenburg
(74) *Attorney, Agent, or Firm* — Frost Brown Todd LLC

(57) ABSTRACT

A guidewire comprises an elongate metal core, an inner layer, an optical core, and an outer layer. The metal core is configured to communicate torsional motion from a proximal end of the metal core to the distal end of the metal core. The inner layer extends about the metal core and has a first index of refraction. The optical core is disposed about the inner layer, wherein the optical core is configured to transmit light along the length of the guidewire. The optical core has a second index of refraction, which is greater than the first index of refraction. The outer layer is disposed about the optical core and has a third index of refraction. The third index of refraction is less than the second index of refraction.

17 Claims, 14 Drawing Sheets

(51) Int. Cl.
   *A61B 5/06*    (2006.01)
   *G02B 23/24*   (2006.01)

(56)         References Cited

U.S. PATENT DOCUMENTS

| | | | |
|---|---|---|---|
| 7,630,676 | B2 | 12/2009 | Pirwitz |
| 7,883,474 | B1 * | 2/2011 | Mirigian ............... A61M 25/09 |
| | | | 600/585 |
| 8,568,304 | B2 | 10/2013 | Vaysar et al. |
| 8,609,125 | B2 * | 12/2013 | Chang .................... A61L 27/34 |
| | | | 424/423 |
| 8,666,209 | B2 * | 3/2014 | Wang ................... A61B 5/0062 |
| | | | 362/572 |
| 8,758,333 | B2 | 6/2014 | Harlan |
| 9,025,598 | B1 * | 5/2015 | Erb .......................... G02B 6/43 |
| | | | 370/389 |
| 9,067,333 | B2 * | 6/2015 | Lippert ............. A61M 25/0009 |
| 9,155,492 | B2 * | 10/2015 | Jenkins .................. A61B 5/065 |
| 9,179,823 | B2 * | 11/2015 | Goldfarb ............ A61B 1/00126 |
| 9,192,307 | B2 * | 11/2015 | Bates .................. A61B 5/0097 |
| 9,193,313 | B2 * | 11/2015 | Erb ........................ B64D 45/00 |
| 9,533,123 | B2 * | 1/2017 | Eberle .................... A61M 25/09 |
| 2008/0228085 | A1 | 9/2008 | Jenkins et al. |
| 2009/0221995 | A1 * | 9/2009 | Harlan ................. A61B 1/0011 |
| | | | 606/7 |
| 2010/0030031 | A1 | 2/2010 | Goldfarb et al. |
| 2011/0004057 | A1 | 1/2011 | Goldfarb et al. |
| 2014/0074141 | A1 | 3/2014 | Johnson et al. |

\* cited by examiner

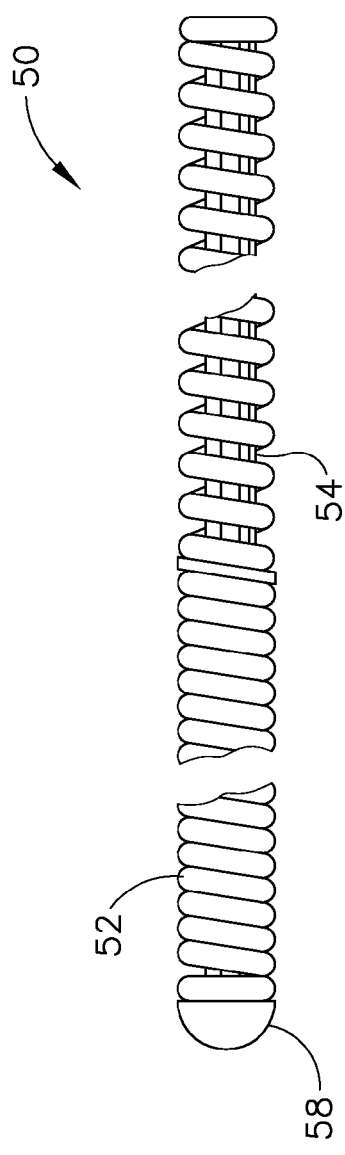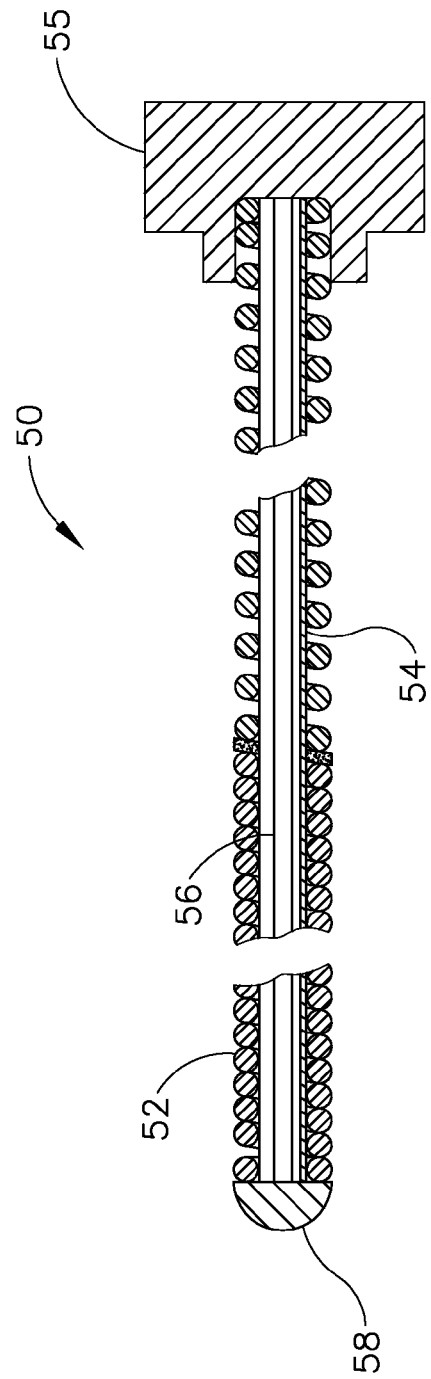
Fig. 3
Fig. 4

MEDICAL GUIDEWIRE WITH INTEGRAL LIGHT TRANSMISSION

PRIORITY

This application claims priority to U.S. Provisional Patent App. No. 62/140,740, entitled "Medical Guidewire with Integral Light Transmission," filed Mar. 31, 2015, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a detailed side elevational view of the illuminating guide wire of FIG. 2A;

FIG. 4 depicts a detailed side cross-sectional view of the illuminating guidewire of FIG. 2A;

Figure 1:
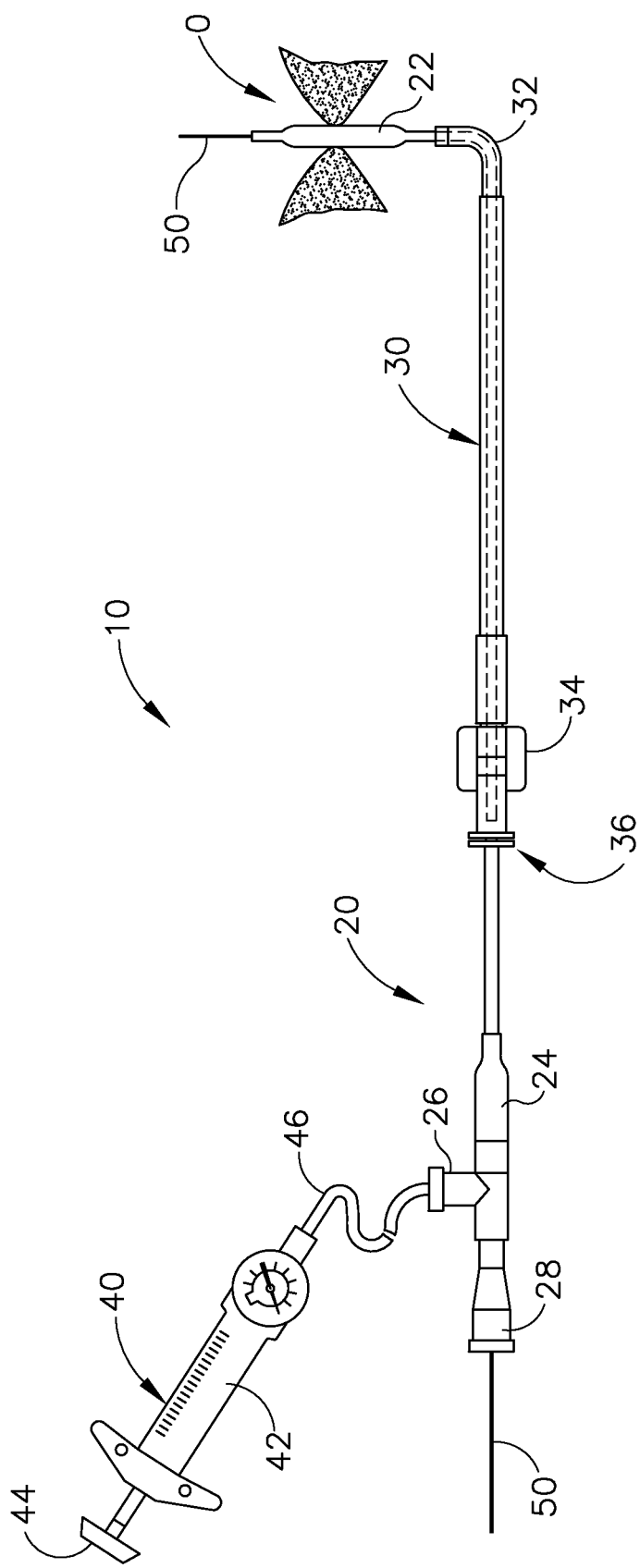
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

Figure 2A:
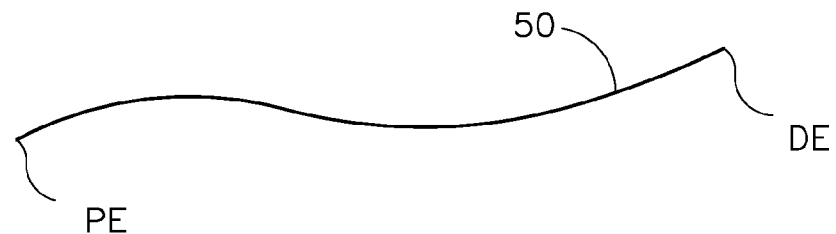
FIG. 2A depicts a side elevational view of an exemplary illuminating guidewire of the dilation catheter system of FIG. 1.
Figure 2B:
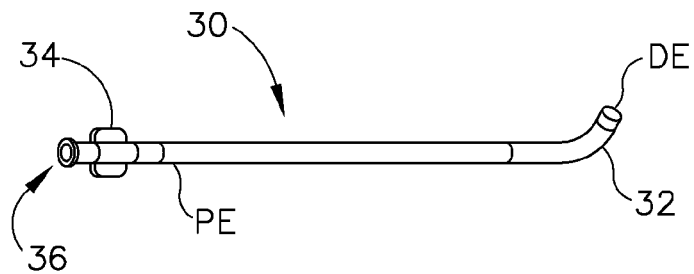
FIG. 2B depicts a side elevational view of an exemplary guide catheter of the dilation catheter system of FIG. 1.
Figure 2C:
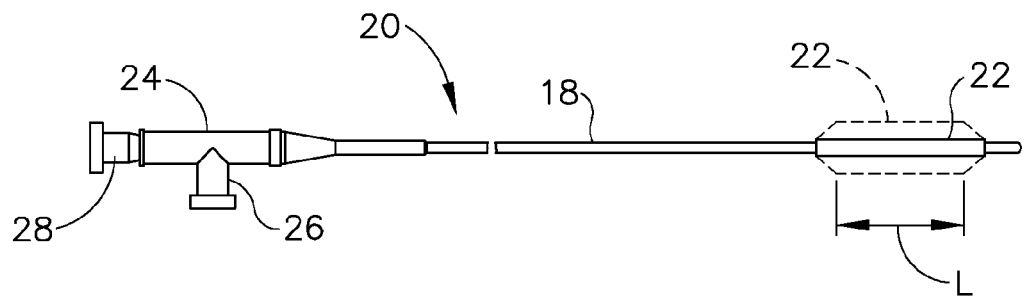
FIG. 2C depicts a side elevational view of an exemplary dilation catheter of the dilation catheter system of FIG. 1.

As best seen in FIG. 2C, the distal end (DE) of dilation catheter (20) includes an inflatable dilator (22). The proximal end (PE) of dilation catheter (20) includes a grip (24), which has a lateral port (26) and an open proximal end (28). A hollow-elongate shaft (18) extends distally from grip. Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, the disclosure of which is incorporated by reference herein.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

II. Overview of Exemplary Endoscope

Figure 5:
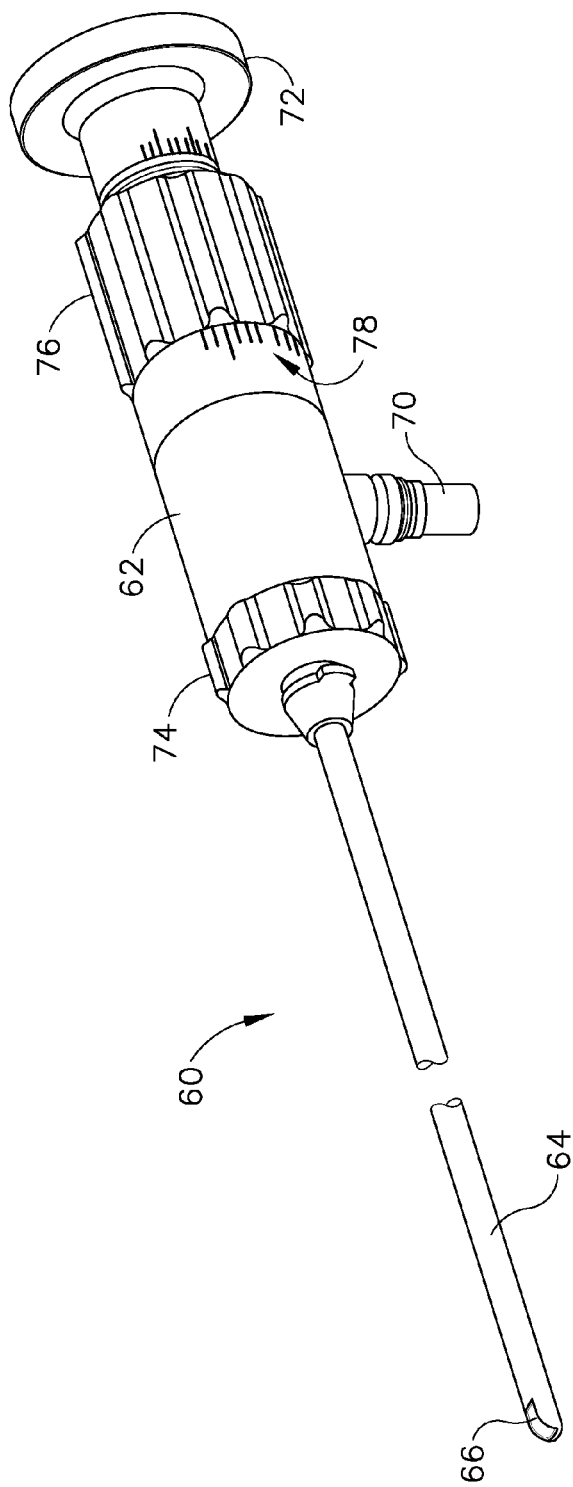
FIG. 5 depicts a perspective view of an exemplary endoscope suitable for use with the dilation catheter system of FIG. 1.
Figure 6:
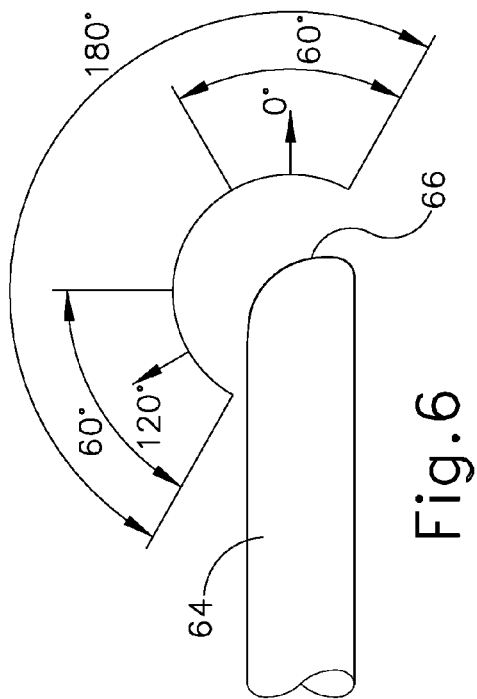
FIG. 6 depicts a side elevational view of the distal end of the endoscope of FIG. 5, showing an exemplary range of viewing angles.

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein III. Exemplary Method for Dilating the Ostium of a Maxillary Sinus FIGS. 7A-7E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 7A:
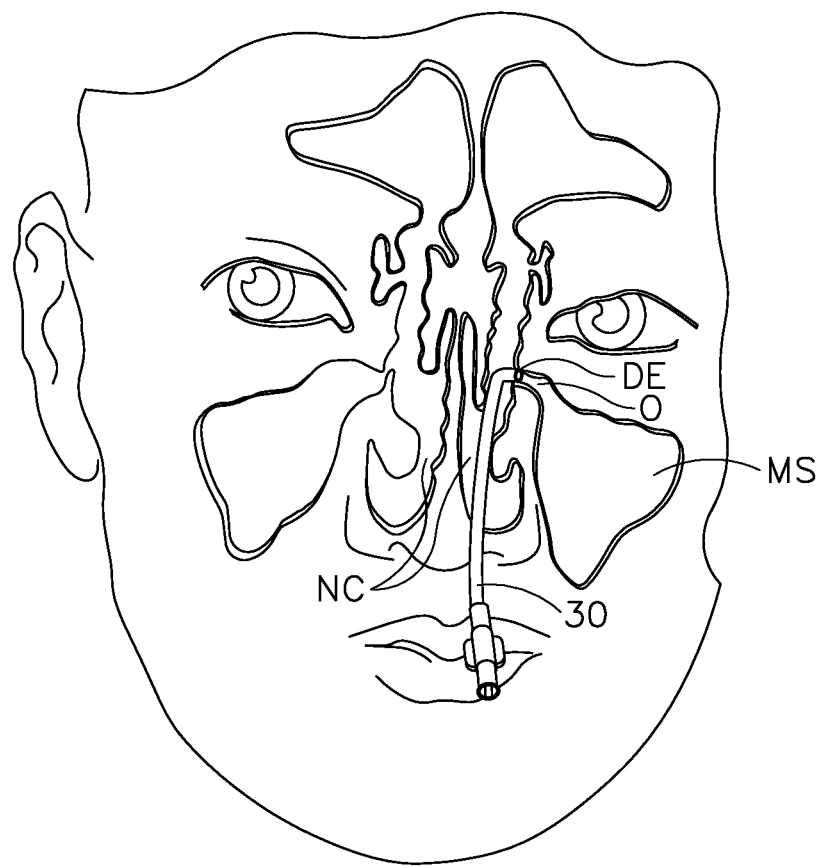
FIG. 7A depicts a front view of the guide catheter of FIG. 2B positioned adjacent an ostium of the maxillary sinus.
Figure 7C:
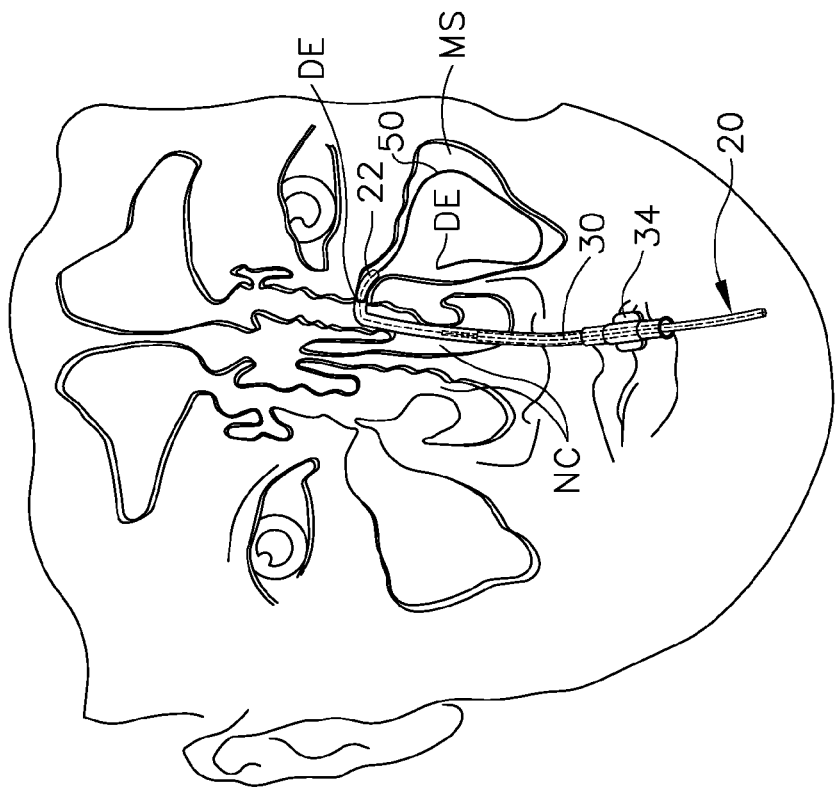
FIG. 7C depicts a front view of the guide catheter of FIG. 2B positioned adjacent an ostium of the maxillary sinus, with the illuminating guidewire of FIG. 2A translated further distally relative to the guide catheter and into the maxillary sinus.
Figure 7B:
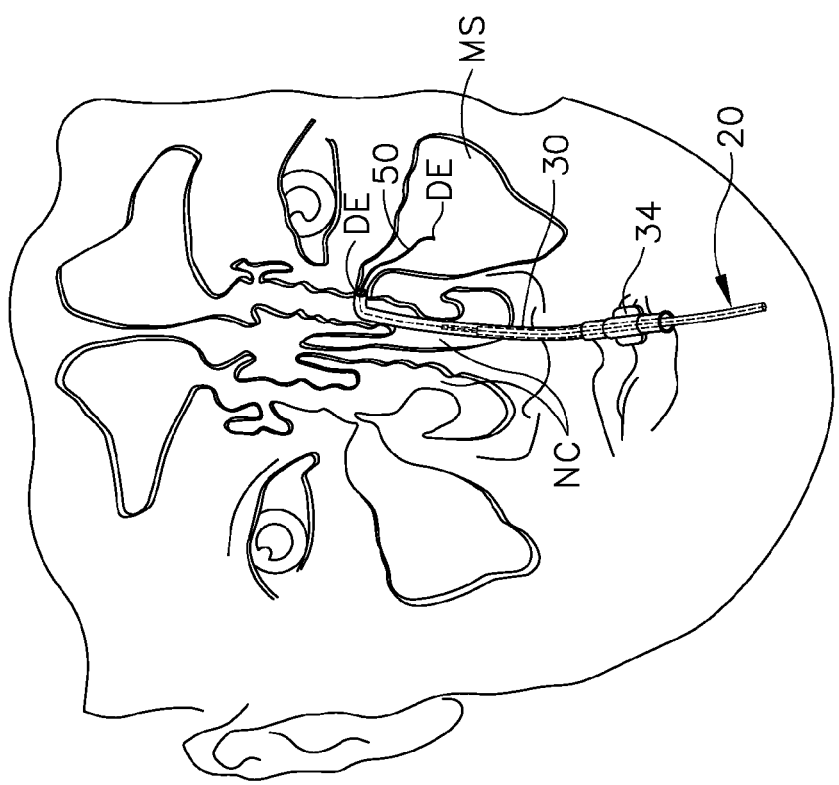
FIG. 7B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus.

In the procedure of the present example, guide catheter (30) may be inserted transnasally and advanced through the nasal cavity (NC) to a position within or near the targeted anatomical passageway to be dilated, the sinus ostium (O), as shown in FIG. 7A. Inflatable dilator (22) and the distal end of guidewire (50) may be positioned within or proximal to bent distal end (32) of guide catheter (30) at this stage. This positioning of guide catheter (30) may be verified endoscopically with an endoscope such as endoscope (60) described above and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 7B and 7C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 7D:
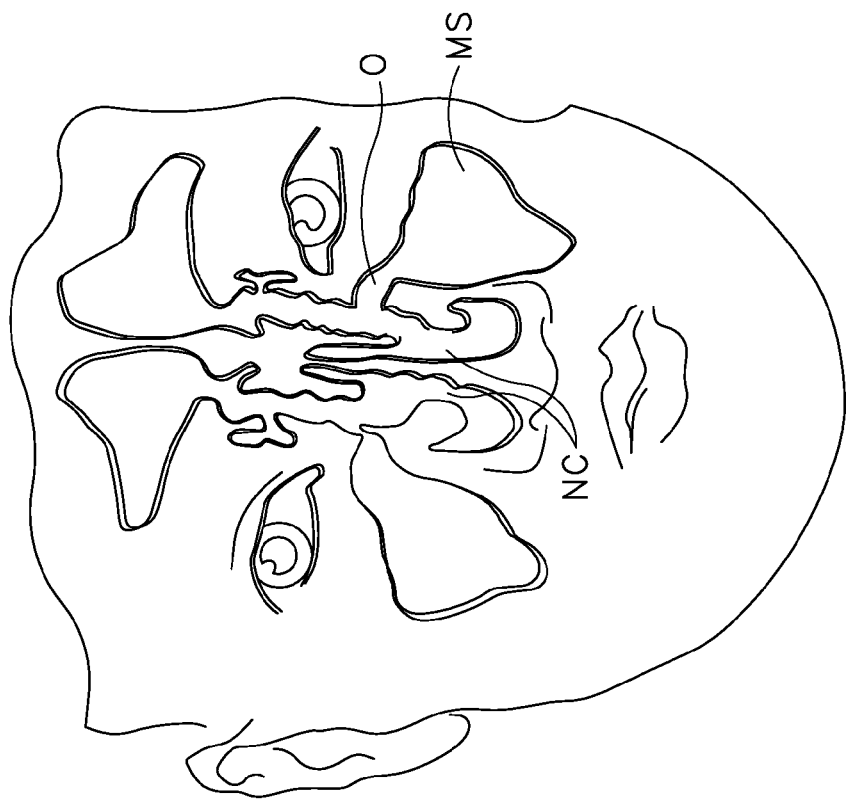
FIG. 7D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.
Figure 7E:
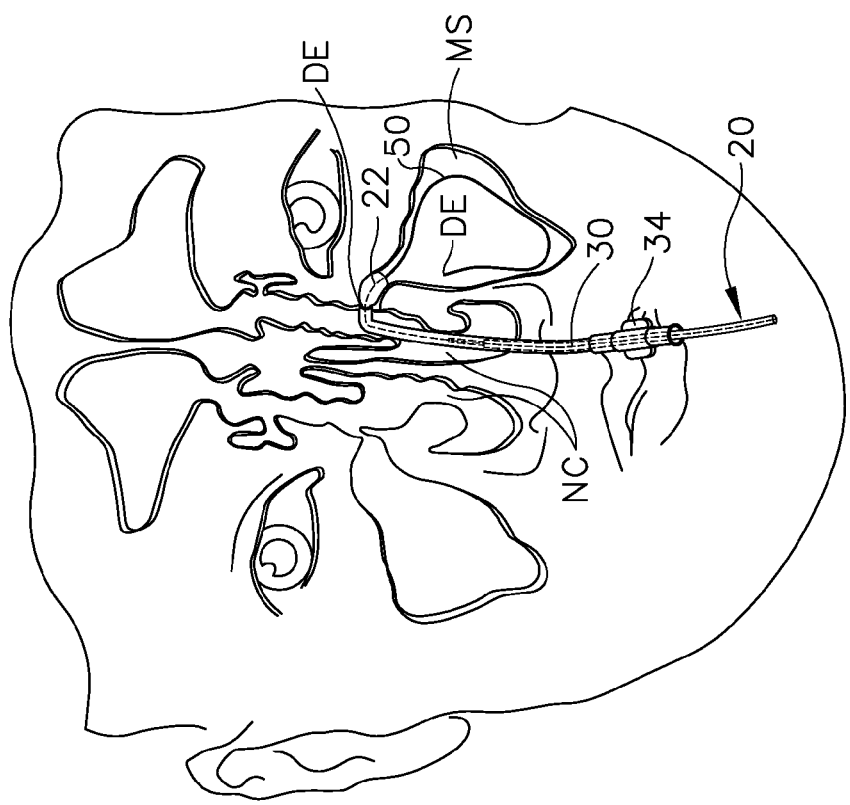
FIG. 7E depicts a front view of an ostium of the maxillary sinus, with the ostium having been enlarged by inflation of the balloon of FIG. 7D.

As shown in FIG. 7C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 7D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 7E.

In some instances, it may be desirable to irrigate the sinus and paranasal cavity after dilation catheter (20) has been used to dilate the ostium (O). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pat. No. 7,630,676, entitled "Methods, Devices and Systems for Treatment and/or Diagnosis of Disorders of the Ear, Nose and Throat," issued Dec. 8, 2009, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

IV. Exemplary Semi-Rigid Illuminating Guidewires

When an operator attempts to rotate or spin a conventional guidewire about the longitudinal axis of the guidewire, the distal end may refrain from rotating during a certain time while the proximal end of the guidewire is being rotated, with an intermediate region of the guidewire storing torsional energy. The guidewire may thus become essentially wound up. At some point, that stored torsional energy may be released and communicated suddenly to the distal end of the guidewire, providing a whipping effect. In some versions of dilation catheter system (10) it may be desirable to provide illuminating guidewire (50) with features that provide at least partial structural rigidity to illuminating guidewire (50) such that, among other forces, torsion applied to guidewire (50) may be communicated along the length of guidewire (50) in an effective manner (e.g., without creating a whipping effect, etc.). For instance, as will be described below, some versions of guidewire (50) may be provided with structural components that extend along the length of guidewire (50) and provide structural rigidity thereto. Various examples of such guidewires will be described in greater detail below; while other examples will be apparent to those of ordinary skill in the art in view of the teachings herein. While the following examples are provided in the context of dilating the ostium (O) of the maxillary sinus (MS) it should be understood that the same examples may be readily applied to the context of dilating the Eustachian tube, other ostia of paranasal sinuses, the frontal recess, and/or other anatomical passageways associated with the ear, nose, and throat.

A. Exemplary Illuminating Guidewire with Adhered Metal Core

Figure 8:
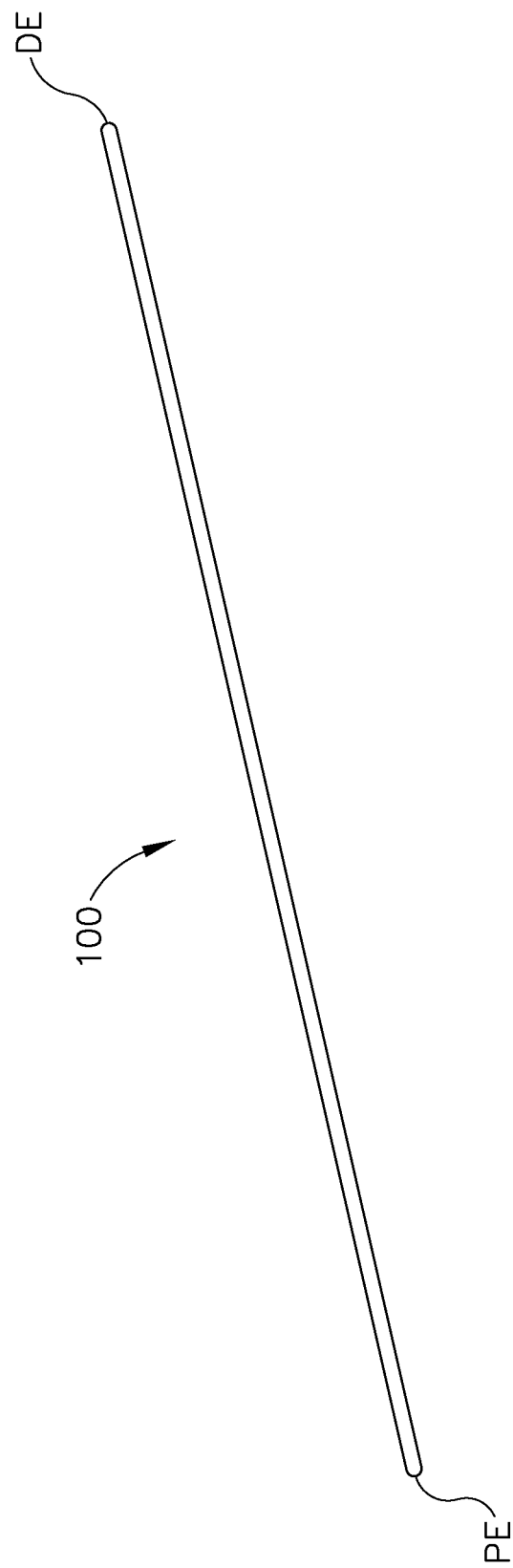
FIG. 8 depicts a perspective view of an exemplary alternative illuminating guidewire suitable for use with the dilation catheter system of FIG. 1.

FIG. 8 shows an exemplary illuminating guidewire (100). Guidewire (100) may be readily incorporated into dilation catheter system (10) in place of guidewire (50). Although guidewire (100) of the present example is depicted as being substantially straight along the entire length of guidewire (100) it should be appreciated that portions of guidewire (100) may have a preformed bend into an angular or curved configuration; or any other appropriate shape. For instance, some versions of guidewire (100) may include a bent proximal portion at the proximal end (PE), a bent distal portion at the distal end (DE), or a bent portion anywhere therebetween.

Figure 9:
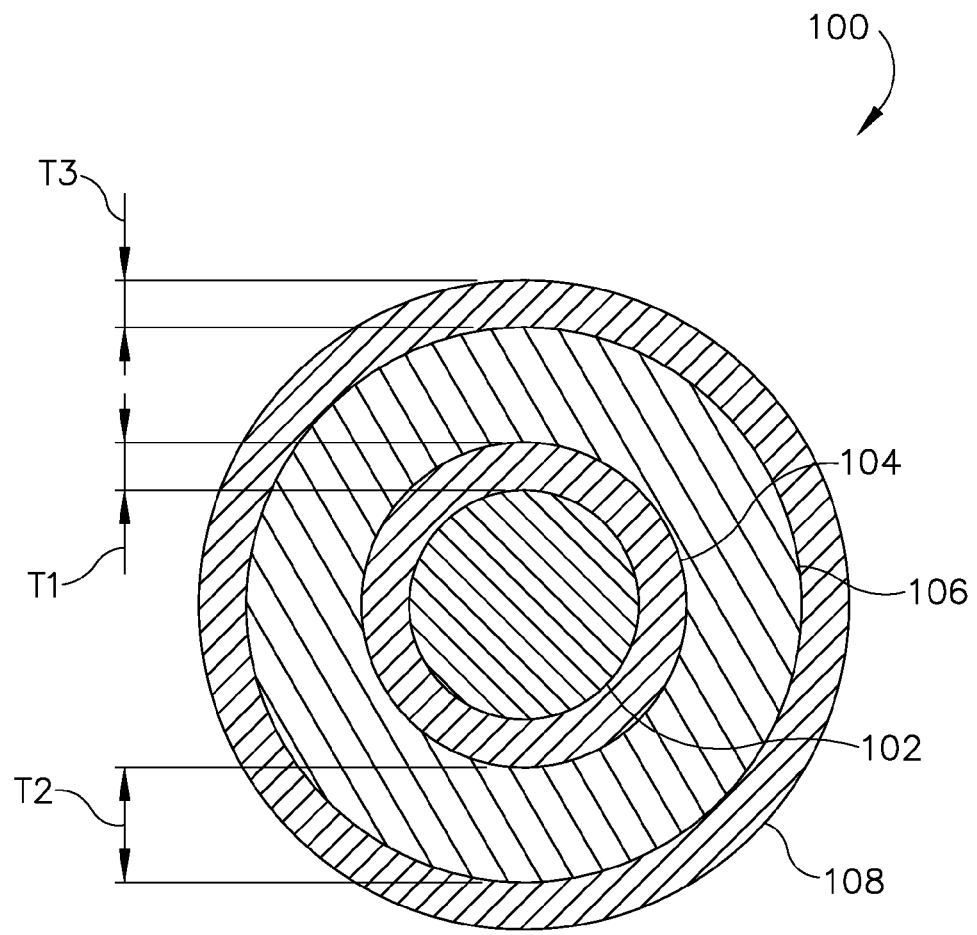
FIG. 9 depicts a cross-sectional end view of the illuminating guidewire of FIG. 8.
Figure 10:
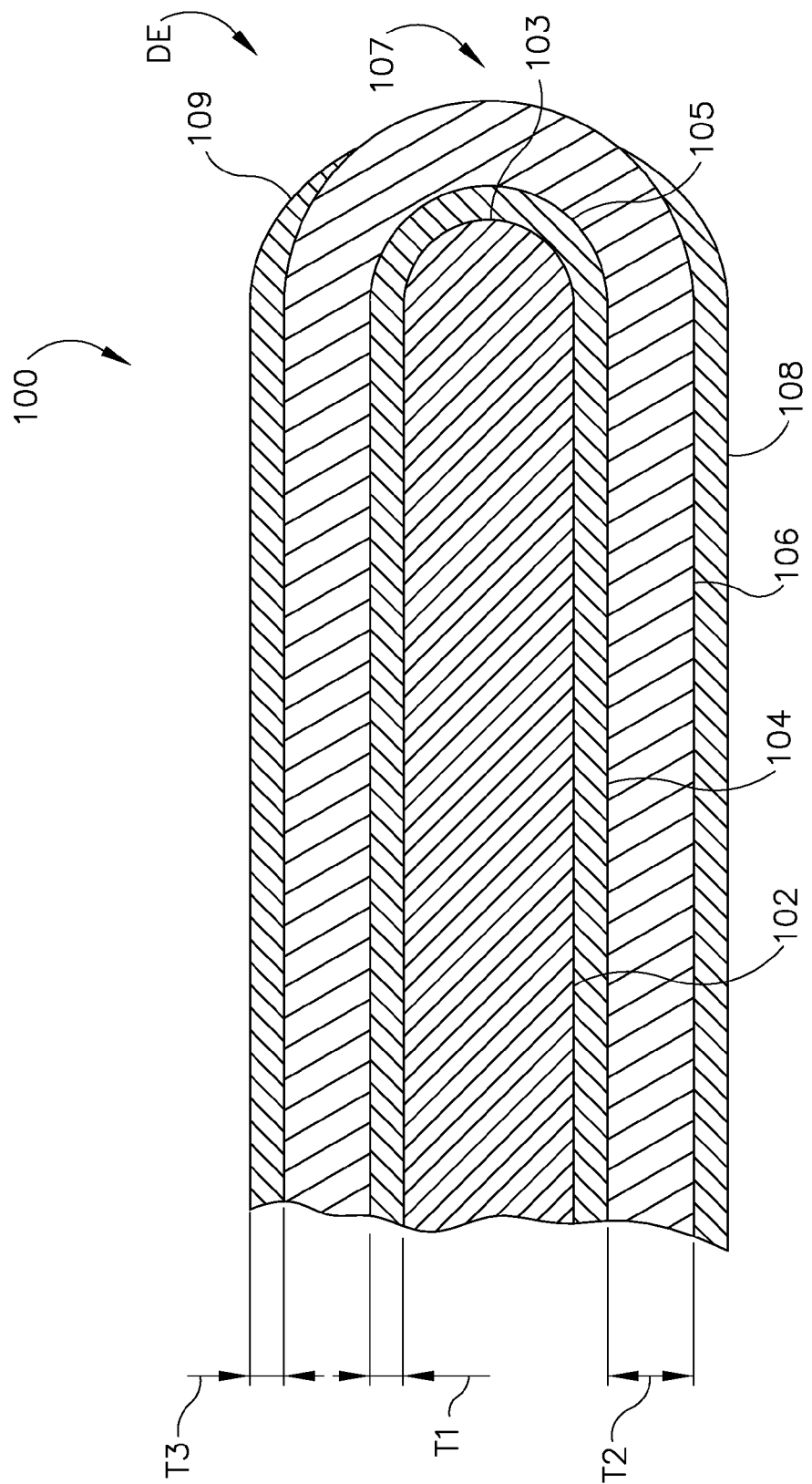
FIG. 10 depicts a cross-sectional side view of a distal end of the illuminating guidewire of FIG. 8.

FIGS. 9 and 10 depict a cross-section of guidewire (100) of the present example. Guidewire (100) of the present example comprises a metal core (102), an inner-polymer layer (104), an optical core layer (106), and an outer-polymer layer (108). Metal core (102) extends substantially the length of guidewire (100) and is configured to provide structural rigidity along the length of guidewire (100) such that, among other forces, torsion applied to guidewire (100) may be effectively and efficiently communicated along the length of guidewire (100). Metal core (102) may comprise any appropriate material including, but not limited to, a super-elastic metal comprising nickel-titanium alloy (e.g., nitinol). If desired, metal core (102) may have progressively increasing flexibility, based on the diameter profile that is ground or otherwise imparted to it.

Inner-polymer layer (104) is coated onto an exterior surface of metal core (102), such that layer (104) is coaxially disposed about core (102) Inner-polymer layer (104) may comprise a material having a relatively low index of refraction (e.g., 1.49) such as optically clear polymethyl methacrylate (PMMA). Alternatively, any other suitable material(s) may be used to form layer (104) as will be appreciated by one of ordinary skill in the art in view of the teachings herein. A thickness (T1) of inner-polymer layer (104) may correlate with a wavelength of light likely to be transmitted along the length of guidewire (100). For instance, inner-polymer layer (104) may have a thickness (T1) of approximately 2.1 micrometers (microns), which corresponds to approximately three times the wavelength of red light (~680 nanometers). Alternatively, inner-polymer layer (104) may have a thickness (T1) of approximately 6.8 micrometers (microns), which corresponds to approximately ten times the wavelength of red light (~680 nanometers). It should be appreciated, however, that inner-polymer layer (104) may have any other appropriate thickness (T1).

Optical core layer (106) is coated onto an exterior surface of inner-polymer layer (104). Optical core layer (106) may have a thickness (T2) of between 100 and 300 micrometers (microns). It should be appreciated, however, that optical core layer (106) may have any other appropriate thickness (T2). Optical core layer (106) may comprise any appropriate material, including, but not limited to, materials having an index of refraction (e.g., 1.59) that is greater than the index of refraction of inner-polymer layer (104) and/or outer-polymer layer (108). In some versions, optical core layer (106) comprises polystyrene. Other suitable materials will be apparent to those of ordinary skill in the art in view of the teachings herein.

Outer-polymer layer (108) is coated onto an exterior surface of optical core layer (106). Outer-polymer layer (108) may comprise a material having a relatively low index of refraction (e.g., 1.49) such as optically clear PMMA and/or any other suitable material(s) as will be appreciated by one of ordinary skill in the art in view of the teachings herein. In some versions of guidewire (100), inner-polymer layer (104) and outer-polymer layer (108) may comprise the same material; while in other versions of guidewire (100), inner-polymer layer (104) and outer-polymer layer (108) may comprise different materials.

A thickness (T3) of outer-polymer layer (108) may correlate with a wavelength of light likely to be transmitted along the length of guidewire (100). For instance, outer-polymer layer (108) may have a thickness (T3) of approximately 2.1 micrometers (microns), which corresponds to approximately three times the wavelength of red light (~680 nanometers). Alternatively, outer-polymer layer (108) may have a thickness (T3) of approximately 6.8 micrometers (microns), which corresponds to approximately ten times the wavelength of red light (~680 nanometers). It should be appreciated, however, that outer-polymer layer (108) may have any other suitable thickness (T3). In some versions of guidewire (100), inner-polymer layer (104) and outer-polymer layer (108) may have the same thickness (T1, T3) and in other versions of guidewire (100), inner-polymer layer (104) and outer-polymer layer (108) may have different thicknesses (T1, T3).

The proximal end of optical core layer (106) may be optically coupled with any suitable light source. Various suitable ways in which optical core layer (106) may be optically coupled a light source, as well as various suitable forms that the light source may take, will be apparent to those of ordinary skill in the art in view of the teachings herein. The materials forming layers (104, 106, 108) may be selected such that the indices of refraction of layers (104, 106, 108) provide total internal reflection (TIR). Thus, light communicated to the proximal end of optical core layer (106) may be refracted and reflected at the interface of layers (104, 106); and also at the interface of layers (106, 108). In other words, light communicated to the proximal end of optical core layer (106) will be communicated along optical core layer (106) to the distal end of optical core layer (106).

As shown in FIG. 10, the distal end (105) of inner-polymer layer (104) fully encompasses the distal end (103) of metal core (102). The distal end (107) of optical core layer (106) fully encompasses distal end (105) of inner-polymer layer (104). Distal end (107) of optical core layer (106) is exposed relative to distal end (109) of outer-polymer layer (108) such that distal end (107) of optical core layer (106) is configured to project light distally from guidewire (100) when optical core layer (106) is illuminated by a light source. In addition, distal end (107) of optical core layer (106) may receive light reflected back from beyond the distal end (DE) of guidewire (100).

The layers (104, 106, 108) of guidewire (100) described above may be formed and/or applied to guidewire (100) by any appropriate method such as dip-coating. In addition, layers (104, 106, 108) of guidewire (100) may be formed and/or applied to guidewire (100) by other methods such as coating extrusion or "over-extrusion." Such extruding may be performed using a crosshead die on a single thermoplastic extruder. Additionally or alternatively, two or more layers (104, 106, 108) of guidewire (100) may be extruded during the same process by using a co-extrusion arrangement in which two or more thermoplastic extruders are coupled to a single crosshead die. In addition to dip-coating and extruding, other processes may be used to form and/or apply layers (104, 106, 108) to guidewire (100) including but not limited to pultrusion, spray, electrostatic spray, or vapor deposition. Other suitable methods that may be used to form guidewire (100) will be apparent to those of ordinary skill in the art in view of the teachings herein. All of these processes (among others) may be used with thermoplastic materials and thermoset materials, such as polyurethane, poly-dimethyl-siloxane, epoxy, etc.

It should be understood from the foregoing that guidewire (100) may be used to provide transillumination through a patient's cheek, some other region of the patient's face, and/or some other region of the patient's anatomy, as described above and as described further in U.S. Pub. No. 2012/0078118, entitled "Sinus Illumination Lightwire Device," published Mar. 29, 2012, the disclosure of which is incorporated by reference herein. When an operator rotates the proximal end (PE) of guidewire (100) about the longitudinal axis of guidewire (100), the distal end (DE) of guidewire (100) may rotate concomitantly in a 1:1 relationship with the (PE), providing a fully efficient and effective transfer of torsional motion. Such results may be provided through the presence and configuration of metal core (102) in combination with the configuration and arrangement of the remaining layers (104, 106, 108) of guidewire (100). Guidewire (100) is capable of performing this torsional transfer in addition to providing communication and projection of light via optical core layer (106), without requiring an additional optical fiber like illumination fiber (56).

B. Exemplary Illuminating Guidewire With Non-Adhered Metal Core

Figure 11:
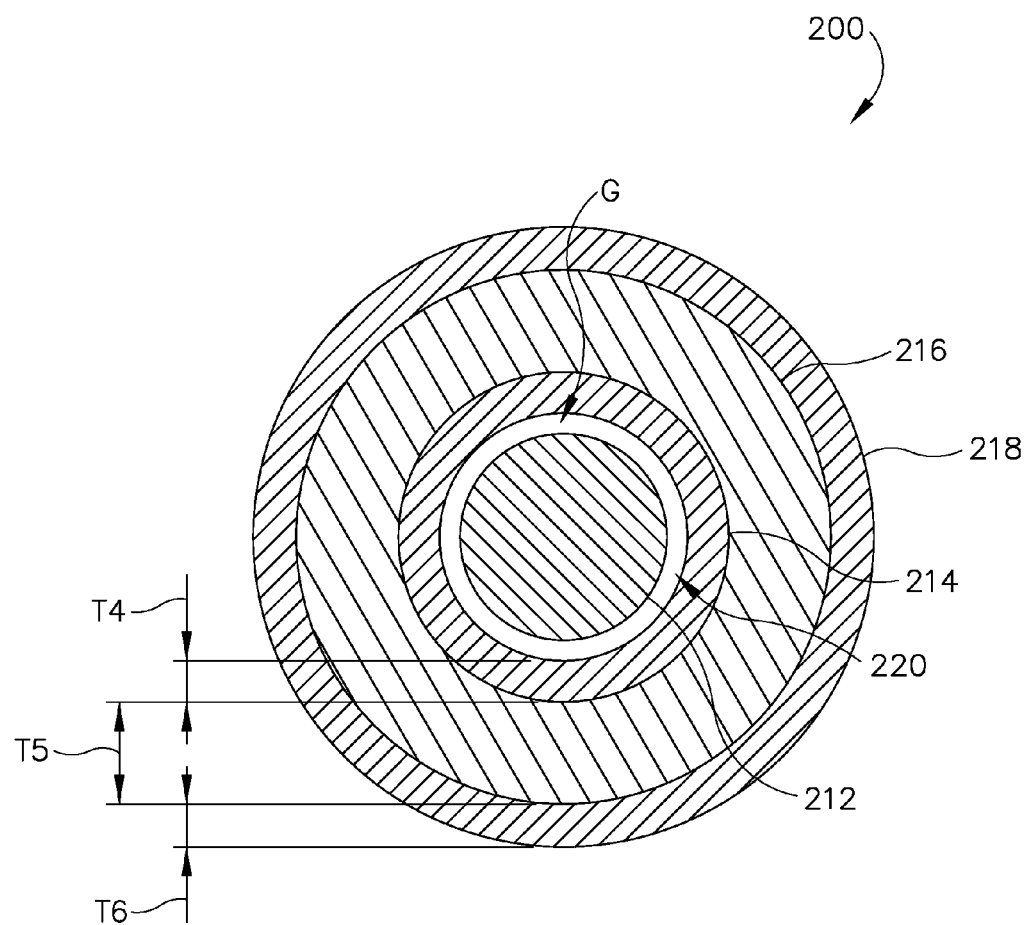
FIG. 11 depicts a cross-sectional end view of another exemplary illuminating guidewire suitable for use with the dilation catheter system of FIG. 1.
Figure 12:
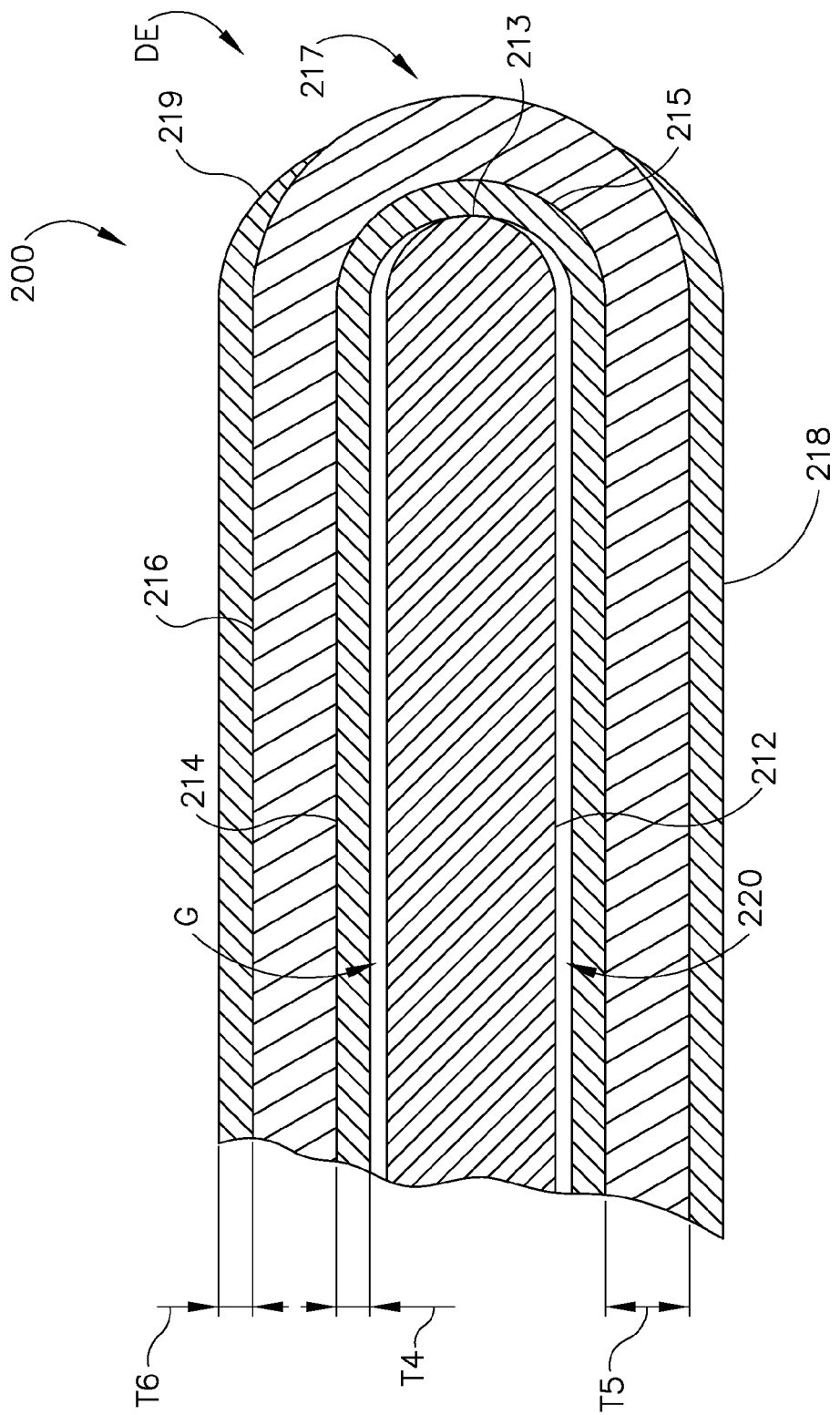
FIG. 12 depicts a cross-sectional side view of a distal end of the illuminating guidewire of FIG. 11.

FIGS. 11 and 12 depict another exemplary guidewire (200), which is similar to guidewire (100) described above and may be readily incorporated into dilation catheter system (10) in place of guidewire (50). Guidewire (200) of the present example comprises a metal core (212), a hollow-polymer layer (214), an optical core layer (216), and an outer-polymer layer (218). Metal core (212) extends substantially the length of guidewire (200) and is configured to provide structural rigidity along the length of guidewire (200) such that, among other forces, torsion applied to guidewire (200) may be effectively and efficiently communicated along the length of guidewire (200). Metal core (202) may comprise any appropriate material including, but not limited to, a super-elastic metal comprising nickel-titanium alloy. If desired, metal core (202) may have progressively increasing flexibility, based on the diameter profile that is ground or otherwise imparted to it.

Hollow-optical layer (214) includes a central lumen (220). Metal core (212) is disposed within central lumen (220) of hollow-optical layer (214). Metal core (212) is sized such that a gap (G) exists between an exterior surface of metal core (212) and an interior surface of hollow-optical layer (214). Hollow-polymer layer (214) may comprise a material having a relatively low index of refraction (e.g., 1.49) such as optically clear polymethyl methacrylate (PMMA). Alternatively, any other suitable material(s) may be used to form layer (214) as will be appreciated by one of ordinary skill in the art in view of the teachings herein. A thickness (T4) of hollow-polymer layer (214) may correlate with a wavelength of light likely to be transmitted along the length of guidewire (200). For instance, hollow-polymer layer (214) may have a thickness (T4) of approximately 2.1 micrometers (microns), which corresponds to approximately three times the wavelength of red light (~680 nanometers). Alternatively, hollow-polymer layer (214) may have a thickness (T4) of approximately 6.8 micrometers (microns), which corresponds to approximately ten times the wavelength of red light (~680 nanometers). It should be appreciated, however, that hollow-polymer layer (214) may have any appropriate thickness (T4).

Optical core layer (216) is coated onto an exterior surface of hollow-polymer layer (214). Optical core layer (216) may have a thickness (T5) of between 100 and 300 micrometers (microns). It should be appreciated, however, that optical core layer (216) may have any appropriate thickness (T5). Optical core layer (216) may comprise any appropriate material, including, but not limited to, materials having an index of refraction (e.g., 1.59) that is greater than the index of refraction of hollow-polymer layer (214) and/or outer-polymer layer (218). In some versions, optical core layer (216) comprises polystyrene. Other suitable materials will be apparent to those of ordinary skill in the art in view of the teachings herein.

Outer-polymer layer (218) is coated onto an exterior surface of optical core layer (216). Outer-polymer layer (218) may comprise a material having a relatively low index of refraction (e.g., 1.49) such as optically clear PMMA and/or any other suitable material(s) as will be appreciated by one of ordinary skill in the art in view of the teachings herein. In some versions of guidewire (200), hollow-polymer layer (214) and outer-polymer layer (218) may comprise the same material; while in other versions of guidewire (200), hollow-polymer layer (214) and outer-polymer layer (218) may comprise different materials.

A thickness (T6) of outer-polymer layer (218) may correlate with a wavelength of light likely to be transmitted along the length of guidewire (200). For instance, outer-polymer layer (218) may have a thickness (T6) of approximately 2.1 micrometers (microns), which corresponds to approximately three times the wavelength of red light (~680 nanometers). Alternatively, outer-polymer layer (218) may have a thickness (T6) of approximately 6.8 micrometers (microns), which corresponds to approximately ten times the wavelength of red light (~680 nanometers). It should be appreciated, however, that outer-polymer layer (218) may have any appropriate thickness (T6). In some versions of guidewire (200), hollow-polymer layer (214) and outer-polymer layer (218) may have the same thickness (T4, T6) and in other versions of guidewire (200), hollow-polymer layer (214) and outer-polymer layer (218) may have different thicknesses (T4, T6).

The proximal end of optical core layer (216) may be optically coupled with any suitable light source. Various suitable ways in which optical core layer (216) may be optically coupled a light source, as well as various suitable forms that the light source may take, will be apparent to those of ordinary skill in the art in view of the teachings herein. The materials forming layers (214, 216, 218) may be selected such that the indices of refraction of layers (214, 216, 218) provide total internal reflection (TIR). Thus, light communicated to the proximal end of optical core layer (216) may be refracted and reflected at the interface of layers (214, 216); and also at the interface of layers (216, 218). In other words, light communicated to the proximal end of optical core layer (216) will be communicated along optical core layer (216) to the distal end of optical core layer (216). Layers (214, 216, 218) thus together define a free-standing hollow optical fiber in this example.

As shown in FIG. 12, the distal end (215) of hollow-polymer layer (214) fully encompasses the distal end (213) of metal core (212). The distal end (217) of optical core layer (216) fully encompasses distal end (215) of hollow-polymer layer (214). Distal end (217) of optical core layer (216) is exposed relative to distal end (219) of outer-polymer layer (218) such that distal end (217) of optical core layer (216) is configured to project light distally from guidewire (200) when optical core layer (216) is illuminated by a light source. In addition, distal end (217) of optical core layer (216) may receive light reflected back from beyond the distal end (DE) of guidewire (200).

The layers (214, 216, 218) of guidewire (200) described above may be formed and/or applied to guidewire (200) by any appropriate method such as dip-coating. In addition, layers (214, 216, 218) of guidewire (200) may be formed and/or applied to guidewire (200) by other methods such as coating extrusion or "over-extrusion." Such extruding may be performed using a crosshead die on a single thermoplastic extruder. Additionally or alternatively, two or more layers (214, 216, 218) of guidewire (200) may be extruded during the same process by using a co-extrusion arrangement in which two or more thermoplastic extruders are coupled to a single crosshead die. In addition to dip-coating and extruding, other processes may be used to form and/or apply layers (214, 216, 218) to guidewire (200) including but not limited to pultrusion, spray, electrostatic spray, or vapor deposition. Other suitable methods that may be used to form guidewire (200) will be apparent to those of ordinary skill in the art in view of the teachings herein. All of these processes (among others) may be used with thermoplastic materials and thermoset materials, such as polyurethane, poly-dimethyl-siloxane, epoxy, etc.

It should be understood from the foregoing that guidewire (200) may be used to provide transillumination through a patient's cheek, some other region of the patient's face, and/or some other region of the patient's anatomy, as described above and as described further in U.S. Pub. No. 2012/0078118, entitled "Sinus Illumination Lightwire Device," published Mar. 29, 2012, the disclosure of which is incorporated by reference herein. When an operator rotates the proximal end (PE) of guidewire (200) about the longitudinal axis of guidewire (100), the distal end (DE) of guidewire (200) may rotate concomitantly in a 1:1 relationship with the (PE), providing a fully efficient and effective transfer of torsional motion. Such results may be provided through the presence and configuration of metal core (202) in combination with the configuration and arrangement of the remaining layers (204, 206, 208) of guidewire (200). Guidewire (200) is capable of performing this torsional transfer in addition to providing communication and projection of light via optical core layer (206), without requiring an additional optical fiber like illumination fiber (56).

Figure 13:
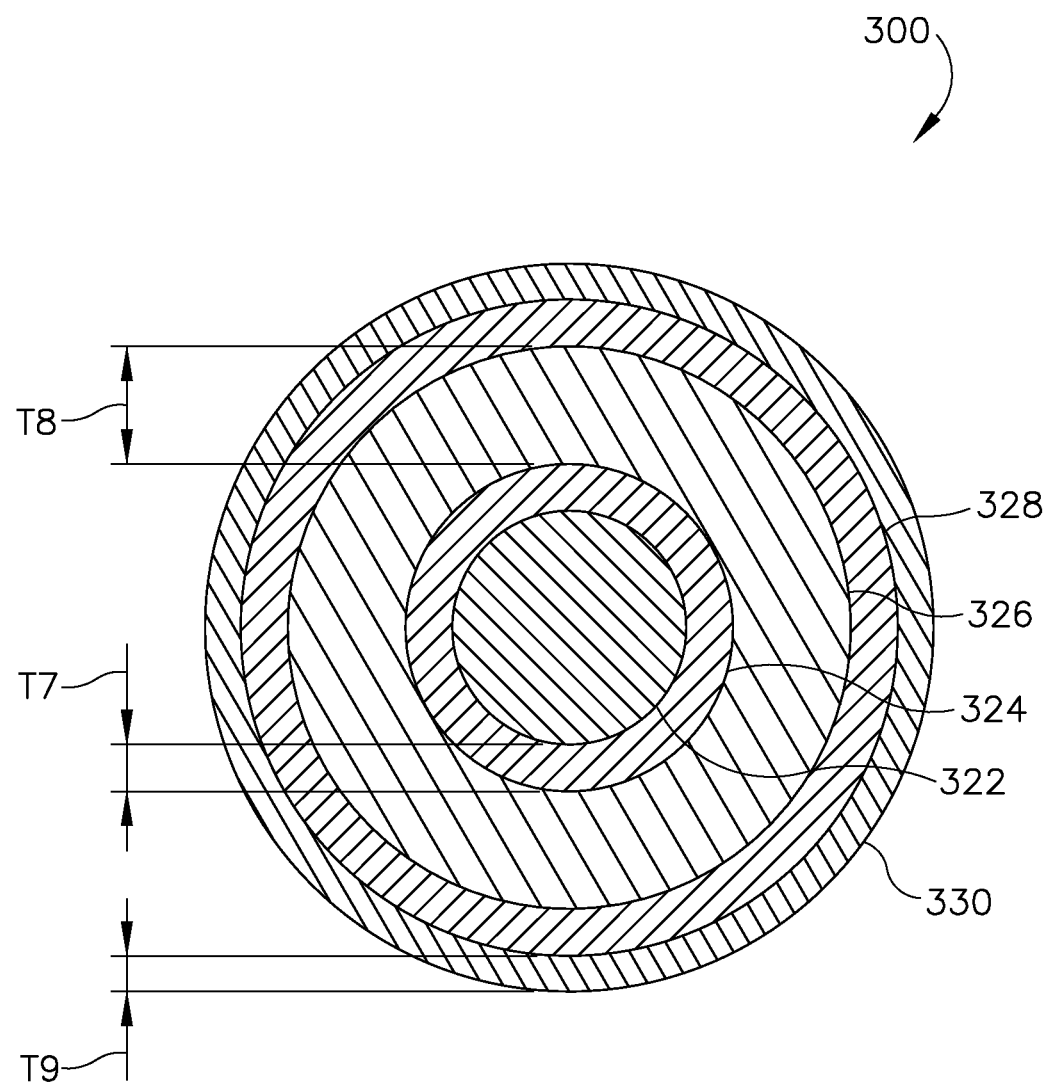
FIG. 13 depicts a cross-sectional end view of yet another exemplary illuminating guidewire suitable for use with the dilation catheter system of FIG. 1.
Figure 14:
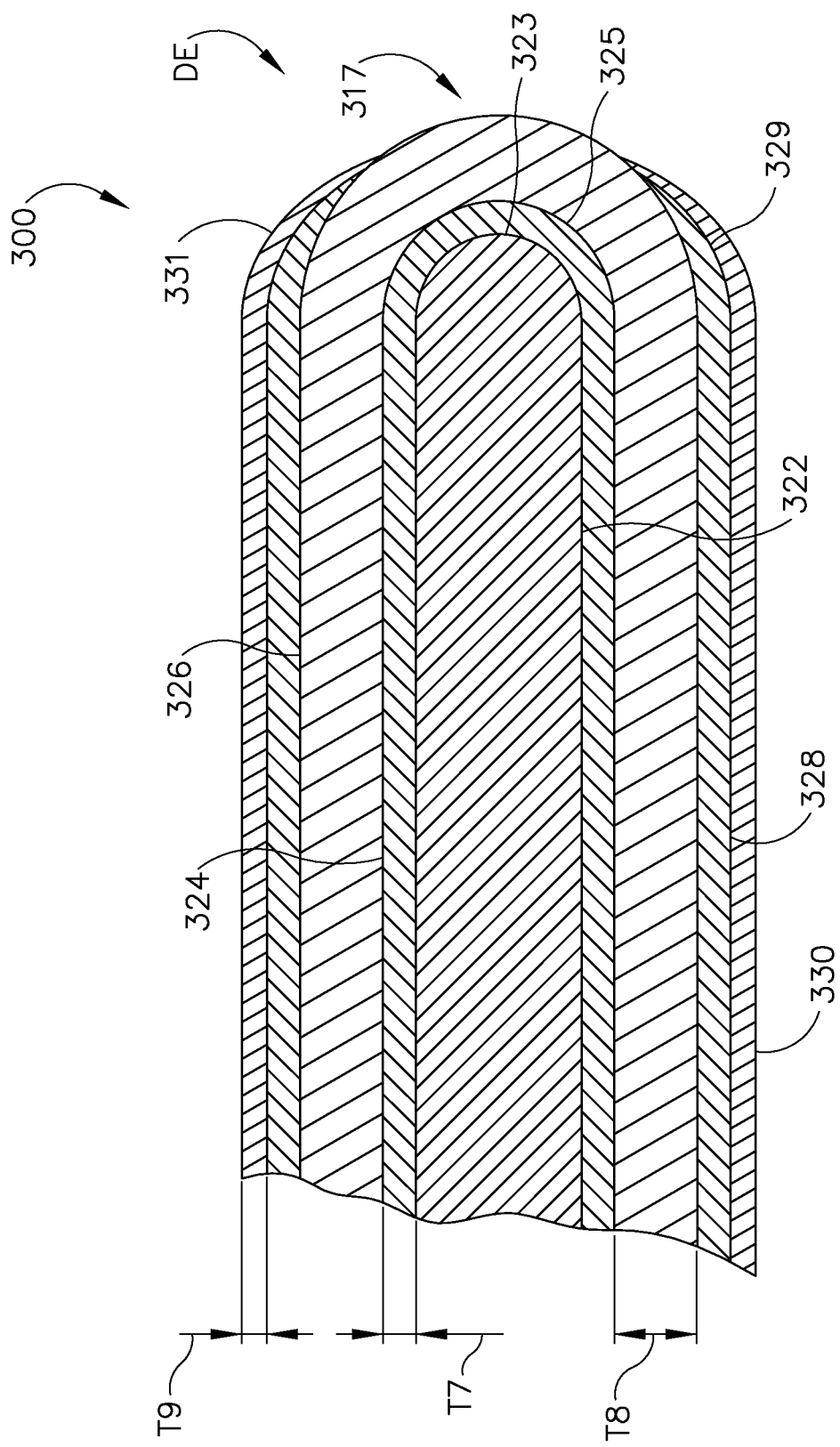
FIG. 14 depicts a cross-sectional side view of a distal end of the illuminating guidewire of FIG. 13.

C. Exemplary Illuminating Guidewire With Adhered Metal Core and Protective Jacket FIGS. 13 and 14 depict another exemplary guidewire (300), which is similar to guidewire (100) described above and may be readily incorporated into dilation catheter system (10) in place of guidewire (50). Guidewire (300) of the present example comprises a metal core (322), an inner-polymer layer (324), an optical core layer (326), an outer-polymer layer (328), and a protective jacket layer (330). Metal core (322) extends substantially the length of guidewire (300) and is configured to provide structural rigidity along the length of guidewire (300) such that, among other forces, torsion applied to guidewire (300) may be effectively and efficiently communicated along the length of guidewire (300). Metal core (322) may comprise any appropriate material including, but not limited to, a super-elastic metal comprising nickel-titanium alloy. If desired, metal core (322) may have progressively increasing flexibility, based on the diameter profile that is ground or otherwise imparted to it.

Inner-polymer layer (324) is coated onto an exterior surface of metal core (322), such that layer (324) is coaxially disposed about core (102) Inner-polymer layer (324) may comprise a material having a relatively low index of refraction (e.g., 1.49) such as optically clear polymethyl methacrylate (PMMA). Alternatively, any other suitable material(s) may be used to form layer (104) as will be appreciated by one of ordinary skill in the art in view of the teachings herein. A thickness (T7) of inner-polymer layer (324) may correlate with a wavelength of light likely to be transmitted along the length of guidewire (300). For instance, inner-polymer layer (324) may have a thickness (T7) of approximately 2.1 micrometers (microns), which corresponds to approximately three times the wavelength of red light (~680 nanometers). Alternatively, inner-polymer layer (324) may have a thickness (T7) of approximately 6.8 micrometers (microns), which corresponds to approximately ten times the wavelength of red light (~680 nanometers). It should be appreciated, however, that inner-polymer layer (324) may have any appropriate thickness (T7).

Optical core layer (326) is coated onto an exterior surface of inner-polymer layer (324). Optical core layer (326) may have a thickness (T8) of between 100 and 300 micrometers (microns). It should be appreciated, however, that optical core layer (326) may have any appropriate thickness (T8). Optical core layer (326) may comprise any appropriate material, including, but not limited to, materials having an index of refraction (e.g., 1.59) that is greater than the index of refraction of inner-polymer layer (324) and/or outer-polymer layer (328). In some versions, optical core layer (326) comprises polystyrene.

Outer-polymer layer (328) is coated onto an exterior surface of optical core layer (326). Outer-polymer layer (328) may comprise a material having a relatively low index of refraction (e.g., 1.49) such as optically clear PMMA and/or any other suitable material(s) as will be appreciated by one of ordinary skill in the art in view of the teachings herein. In some versions of guidewire (300), inner-polymer layer (324) and outer-polymer layer (328) may comprise the same material; while in other versions of guidewire (300), inner-polymer layer (324) and outer-polymer layer (328) may comprise different materials.

A thickness (T9) of outer-polymer layer (328) may correlate with a wavelength of light likely to be transmitted along the length of guidewire (300). For instance, outer-polymer layer (328) may have a thickness (T9) of approximately 2.1 micrometers (microns), which corresponds to approximately three times the wavelength of red light (~680 nanometers). Alternatively, outer-polymer layer (328) may have a thickness (T9) of approximately 6.8 micrometers (microns), which corresponds to approximately ten times the wavelength of red light (~680 nanometers). It should be appreciated, however, that outer-polymer layer (328) may have any appropriate thickness (T9). In some versions of guidewire (300), inner-polymer layer (324) and outer-polymer layer (328) may have the same thickness (T7, T9) and in other versions of guidewire (300), inner-polymer layer (324) and outer-polymer layer (328) may have different thicknesses (T7, T9).

Protective jacket layer (330) is coated onto an exterior surface of outer-polymer layer (328). Jacket layer (330) may comprise any appropriate material including, but not limited to, thermoplastics, such as nylon, polyether block amide (e.g., PEBAX® by Arkema), or polyurethane, as well as thermosets, such as polydimethylsiloxane. It should be understood that jacket layer (330) of the present example may be applied to any of the other versions of guidewire (100, 200) discussed above.

The proximal end of optical core layer (326) may be optically coupled with any suitable light source. Various suitable ways in which optical core layer (326) may be optically coupled a light source, as well as various suitable forms that the light source may take, will be apparent to those of ordinary skill in the art in view of the teachings herein. The materials forming layers (324, 326, 328) may be selected such that the indices of refraction of layers (324, 326, 328) provide total internal reflection (TIR). Thus, light communicated to the proximal end of optical core layer (326) may be refracted and reflected at the interface of layers (324, 326); and also at the interface of layers (326, 328). In other words, light communicated to the proximal end of optical core layer (326) will be communicated along optical core layer (326) to the distal end of optical core layer (326).

As shown in FIG. 14, the distal end (325) of inner-polymer layer (324) fully encompasses the distal end (323) of metal core (322). The distal end (327) of optical core layer (326) fully encompasses distal end (325) of inner-polymer layer (324). Distal end (327) of optical core layer (326) is exposed relative to distal end (329) of outer-polymer layer (328) and distal end (331) of jacket layer (330) of such that distal end (327) of optical core layer (326) is configured to project light distally from guidewire (300) when optical core layer (326) is illuminated by a light source. In addition, distal end (307) of optical core layer (326) may receive light reflected back from beyond the distal end (DE) of guidewire (300).

The layers (324, 326, 328, 330) of guidewire (300) described above may be formed and/or applied to guidewire (300) by any appropriate method such as dip-coating. In addition, layers (324, 326, 328, 330) of guidewire (300) may be formed and/or applied to guidewire (300) by other methods such as coating extrusion or "over-extrusion." Such extruding may be performed using a crosshead die on a single thermoplastic extruder. Additionally or alternatively, two or more layers (324, 326, 328, 330) of guidewire (300) may be extruded during the same process by using a co-extrusion arrangement in which two or more thermoplastic extruders are coupled to a single crosshead die. In addition to dip-coating and extruding, other processes may be used to form and/or apply layers (324, 326, 328, 330) to guidewire (300) including but not limited to pultrusion, spray, electrostatic spray, or vapor deposition. Other suitable methods that may be used to form guidewire (300) will be apparent to those of ordinary skill in the art in view of the teachings herein. All of these processes (among others) may be used with thermoplastic materials and thermoset materials, such as polyurethane, poly-dimethyl-siloxane, epoxy, etc.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A guidewire comprising: (a) an elongate metal core, wherein the metal core has a proximal end and a distal end, wherein the metal core is configured to communicate torsional motion from the proximal end to the distal end; (b) an inner layer extending about the metal core, wherein the inner layer has a first index of refraction; (c) an optical core, wherein the optical core is disposed about the inner layer, wherein the optical core is configured to transmit light along the length of the guidewire, wherein the optical core has a second index of refraction, wherein the second index of refraction is greater than the first index of refraction; and (d) an outer layer, wherein the outer layer is disposed about the optical core, wherein the outer layer has a third index of refraction, wherein the third index of refraction is less than the second index of refraction.

EXAMPLE 2

The guidewire of Example 1, wherein a distal end of the optical core is exposed relative to the outer layer.

EXAMPLE 3

The guidewire of any one or more of Examples 1 through 2, wherein a thickness of the inner layer is between 2.1 micrometers and 6.8 micrometers.

EXAMPLE 4

The guidewire of any one or more of Examples 1 through 3, wherein a thickness of the outer layer is between 2.1 micrometers and 6.8 micrometers.

EXAMPLE 5

The guidewire of any one or more of Examples 1 through 4, wherein a thickness of the optical core is between 100 micrometers and 300 micrometers.

EXAMPLE 6

The guidewire of any one or more of Examples 1 through 5, wherein the inner layer defines a central lumen.

EXAMPLE 7

The guidewire of Example 6, wherein the metal core is disposed within the central lumen of the inner layer.

EXAMPLE 8

The guidewire of any one or more of Examples 6 through 7, wherein a gap exists between an exterior surface of the metal core and an interior surface of the central lumen of the inner layer.

EXAMPLE 9

The guidewire of any one or more of Examples 1 through 8, wherein the third index of refraction is equal to the first index of refraction.

EXAMPLE 10

The guidewire of any one or more of Examples 1 through 9, wherein the inner layer and the outer layer comprise the same kind of material.

EXAMPLE 11

The guidewire of any one or more of Examples 1 through 10, wherein the metal core comprises nickel-titanium alloy.

EXAMPLE 12

The guidewire of any one or more of Examples 1 through 11, wherein the inner layer comprises polymethyl methacrylate.

EXAMPLE 13

The guidewire of any one or more of Examples 1 through 12, wherein the optical core comprises polystyrene.

EXAMPLE 14

The guidewire of any one or more of Examples 1 through 13, further comprising a jacket layer disposed about the outer layer.

EXAMPLE 15

The guidewire of Example 14, wherein the jacket layer comprises a thermoplastic or thermoset material.

EXAMPLE 16

The guidewire of any one or more of Examples 14 through 15, wherein a distal end of the optical core is exposed relative to the jacket layer.

EXAMPLE 17

The guidewire of any one or more of Examples 1 through 16, wherein the guidewire has an outer diameter configured to fit within an ostium of a paranasal sinus.

EXAMPLE 18

A guidewire comprising: (a) an elongate metal core, wherein the metal core has a proximal end and a distal end, wherein the metal core is configured to communicate torsional motion from the proximal end to the distal end; and (b) at least one light-transmitting layer, wherein the at least one light-transmitting layer is disposed about the metal core, wherein the at least one light-transmitting layer is configured to transmit light along the length of the guidewire.

EXAMPLE 19

The guidewire of Example 18, wherein the at least one light-transmitting layer defines a hollow optical fiber coaxially positioned about the metal core.

EXAMPLE 20

A guidewire comprising: (a) an elongate metal core, wherein the metal core has a proximal end and a distal end, wherein the metal core is configured to communicate torsional motion from the proximal end to the distal end; (b) an inner layer, wherein the inner layer is disposed about the metal core, wherein the inner layer defines a central lumen, wherein the metal core is disposed within the central lumen of the inner layer, wherein a gap exists between an exterior surface of the metal core and an interior surface of the central lumen of the inner layer; (c) an optical core, wherein the optical core is disposed about the inner layer, wherein the optical core is configured to transmit light along the length of the guidewire; and (d) an outer layer, wherein the outer layer is disposed about the optical core.

VI. Miscellaneous

While various examples of optically transmissive materials are noted above, it should be understood that any of the materials listed in the below table (among other various materials) may be used in addition to or in lieu of those materials listed above. Various suitable combinations (based on index of refraction, among other considerations) will be apparent to those of ordinary skill in the art in view of the teachings herein.

| Material Name | Material Type | Index of Refraction |
| --- | --- | --- |
| ULTEM 1000 | Polyetherimide | 1.67 |
| (poly) carbonate | (poly) carbonate | 1.58 |
| (poly) methyl methacrylate (PMMA) | Acrylic | 1.49 |
| Radel R (R-5XXX) | Polysulfone | 1.672 |
| Polypropylene | Polypropylene | 1.49 |
| PVDF | PVDF | 1.42 |
| TPX or PMP | Polymethylpentene | 1.463 |
| FEP | Fluorinated ethylene propylene | 1.344 |
| PETG | PETG | 1.57 |
| (poly) styrene | (poly) styrene | 1.59 |
| THV 2030G | Fluoropolymer blend | 1.35 |
| THV 220G | Fluoropolymer blend | 1.36 |
| THV 500G | Fluoropolymer blend | 1.35 |
| Udel P3700 HC (High Clarity) | Polysulfone | 1.635 |
| Udel P3703 NT 05 | Polysulfone | 1.635 |
| Udel P3500 | Polysulfone | 1.63 |
| Zeonex 330R | COP | 1.509 |
| Zeonex 480 | COP | 1.525 |
| Zeonex 480R | COP | 1.525 |
| Zeonex 690R | COP | 1.530 |
| Zeonex E48R | COP | 1.530 |
| Zeonor 1020R | COP | 1.53 |
| Zeonor 1420R | COP | 1.53 |
| Zeonor 1600 | COP | 1.53 |

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/ replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A guidewire comprising:
    (a) an elongate metal core, wherein the metal core has a proximal end and a distal end, wherein the metal core is configured to communicate torsional motion from the proximal end to the distal end;
    (b) an inner layer extending about the metal core, wherein the inner layer has a first index of refraction;
    (c) an optical core, wherein the optical core is disposed about the inner layer, wherein the optical core is configured to transmit light along the length of the guidewire, wherein the optical core has a second index of refraction, wherein the second index of refraction is greater than the first index of refraction; and
    (d) an outer layer, wherein the outer layer is disposed about the optical core, wherein the outer layer has a third index of refraction, wherein the third index of refraction is less than the second index of refraction.

2. The guidewire of claim 1, wherein a distal end of the optical core is exposed relative to the outer layer.

3. The guidewire of claim 1, wherein a thickness of the inner layer is between 2.1 micrometers and 6.8 micrometers.

4. The guidewire of claim 1, wherein a thickness of the outer layer is between 2.1 micrometers and 6.8 micrometers.

5. The guidewire of claim 1, wherein a thickness of the optical core is between 100 micrometers and 300 micrometers.

6. The guidewire of claim 1, wherein a gap exists between an exterior surface of the metal core and an interior surface of the central lumen of the inner layer.

7. The guidewire of claim 1, wherein the third index of refraction is equal to the first index of refraction.

8. The guidewire of claim 1, wherein the inner layer and the outer layer comprise the same kind of material.

9. The guidewire of claim 1, wherein the metal core comprises nickel-titanium alloy.

10. The guidewire of claim 1, wherein the inner layer comprises polymethyl methacrylate.

11. The guidewire of claim 1, wherein the optical core comprises polystyrene.

12. The guidewire of claim 1, further comprising a jacket layer disposed about the outer layer.

13. The guidewire of claim 12, wherein the jacket layer comprises a thermoplastic or thermoset material.

14. The guidewire of claim 12, wherein a distal end of the optical core is exposed relative to the jacket layer.

15. The guidewire of claim 1, wherein the guidewire has an outer diameter configured to fit within an ostium of a paranasal sinus.

16. A guidewire comprising:
    (a) an elongate metal core, wherein the metal core has a proximal end and a distal end, wherein the metal core is configured to communicate torsional motion from the proximal end to the distal end; and
    (b) at least one light-transmitting layer, wherein the at least one light-transmitting layer is coaxially disposed about the metal core, wherein the at least one light-transmitting layer is configured to transmit light along the length of the guidewire.

17. The guidewire of claim 16, wherein the at least one light-transmitting layer defines a hollow optical fiber coaxially positioned about the metal core.

* * * * *